United States Patent
O'Brien (10) Patent No.: US 11,883,230 B2
(45) Date of Patent: Jan. 30, 2024

(54) METHOD AND APPARATUS FOR MALARIAL-NEUROLOGIC-INJURY-MECHANISM DIAGNOSIS

(71) Applicant: Research Institute at Nationwide Children's Hospital, Columbus, OH (US)

(72) Inventor: Nicole Fortier O'Brien, Bexley, OH (US)

(73) Assignee: The Research Institute at Nationwide Children's Hospital, Columbus, OH (US)

( * ) Notice: Subject to any disclaimer, the term of this patent is extended or adjusted under 35 U.S.C. 154(b) by 232 days.

(21) Appl. No.: 16/641,280

(22) PCT Filed: Sep. 18, 2018

(86) PCT No.: PCT/US2018/051451
§ 371 (c)(1),
(2) Date: Feb. 24, 2020

(87) PCT Pub. No.: WO2019/060279
PCT Pub. Date: Mar. 28, 2019

(65) Prior Publication Data
US 2020/0178925 A1 Jun. 11, 2020

Related U.S. Application Data

(60) Provisional application No. 62/562,069, filed on Sep. 22, 2017.

(51) Int. Cl.
*A61B 8/08* (2006.01)
*A61B 8/06* (2006.01)

(52) U.S. Cl.
CPC .............. *A61B 8/0808* (2013.01); *A61B 8/06* (2013.01); *A61B 8/488* (2013.01); *A61B 8/5223* (2013.01); *A61B 2576/026* (2013.01)

(58) Field of Classification Search
CPC ......... A61B 8/0808; A61B 8/06; A61B 8/488; A61B 8/5223; A61B 2576/026;
(Continued)

(56) References Cited

U.S. PATENT DOCUMENTS 5,379,770 A 1/1995 Van Veen
2004/0230124 A1* 11/2004 Querfurth .............. A61B 5/031
600/485

(Continued)

FOREIGN PATENT DOCUMENTS

WO WO 2015/073903 5/2015
WO WO 2017/181029 10/2017

OTHER PUBLICATIONS

Henry, Michael MD, et al. "Pseudotumor Cerebri in Children With Sickle Cell Disease: A Case 1-7 Series" Pediatrics vol. 113 No. 3 Mar. 2004. Retrieved on [Dec. 13, 2018] (7 pages).
(Continued)

*Primary Examiner* — Bo Joseph Peng (57) ABSTRACT

A transcranial scanning device and method of use is disclosed. The transcranial scanning device is for identifying a neurologic-injury-mechanism and comprises a sensing wand comprising a transducer that produces and receives sound waves. The sensing wand is passed over a head of a patent with cerebral malaria, and sound waves reflect off of blood cells in blood vessels in the head of the patient creating an output sound wave responsive to a blood flow of the patient. The output sound wave is received by the transducer. An output screen coupled to the sensing wand, displays in real time an output waveform corresponding to the output sound wave, wherein the output waveform is indicative of one or more symptoms of cerebral malaria, and wherein said symptoms identify one or more neurologic-injury-mechanism occurring within the patient.

20 Claims, 8 Drawing Sheets

(58) Field of Classification Search
CPC ...... A61B 8/4227; Y02A 50/30; Y02A 90/10; G16H 50/30
See application file for complete search history.

(56) References Cited

U.S. PATENT DOCUMENTS

| | | | | |
|---|---|---|---|---|
| 2006/0265022 A1* | 11/2006 | John | ................ | A61N 2/006 607/45 |
| 2006/0287600 A1 | 12/2006 | McEowen | | |
| 2010/0204589 A1 | 8/2010 | Swoboda et al. | | |
| 2010/0249597 A1 | 9/2010 | Shi | | |
| 2011/0172545 A1* | 7/2011 | Grudic | ................ | G16H 50/50 600/485 |
| 2011/0201962 A1* | 8/2011 | Grudic | ................ | G16H 40/60 600/561 |
| 2011/0282169 A1* | 11/2011 | Grudic | ................ | G06N 20/00 600/371 |
| 2012/0022377 A1 | 1/2012 | Chin et al. | | |
| 2014/0371545 A1* | 12/2014 | Ben-Ari | ................ | A61B 5/031 600/301 |
| 2017/0065193 A1* | 3/2017 | Yu | ................ | A61B 5/6885 |
| 2017/0086682 A1* | 3/2017 | Johnson | ................ | A61B 5/7425 |
| 2019/0015052 A1* | 1/2019 | Scalzo | ................ | G06K 9/00516 |

OTHER PUBLICATIONS

International Search Report and Written Opinion dated Jan. 4, 2019 (13 pages).

* cited by examiner

METHOD AND APPARATUS FOR MALARIAL-NEUROLOGIC-INJURY-MECHANISM DIAGNOSIS

CROSS REFERENCE TO RELATED APPLICATIONS

The following is a U.S. National phase patent application filed under 35 U.S.C. 371 claiming priority to international patent application serial number PCT/US18/51451 having a filing date of Sep. 18, 2018 and was published by the International Bureau as publication number WO 2019/060279 on Mar. 28, 2019 which claims priority to U.S. Provisional Patent Application Ser. No. 62/562,069 filed Sep. 22, 2017 entitled METHOD AND APPARATUS FOR MALARIAL-NEUROLOGIC-INJURY-MECHANISM DIAGNOSIS. All of the above-identified applications and publications from which priority is claimed are herein incorporated by reference in their entireties for all purposes.

FIELD OF THIS DISCLOSURE

The present disclosure relates to method and apparatus for identifying a mechanism of neurologic injury in persons having cerebral malaria. More specifically, the present disclosure relates to identifying a mechanism of neurologic injury in persons having cerebral malaria using a transcranial sensing apparatus, such as a trans-cranial Doppler ultrasound, and identifying a treatment type based upon the mechanism that is identified.

BACKGROUND

Worldwide, malaria affects two million individuals annually and has resulted in more than 500,000 deaths, primarily in Africa. Cerebral malaria is the most severe neurological manifestation of malaria with case fatality rates ranging from 15-40%. Survivors of childhood cerebral malaria often sustain significant brain injury with long-term neurologic deficits in gross motor function, sensory function, cognition, and behavior apparent in 11-30% of cases. As such, cerebral malaria is the leading cause of neuro-disability in African children.

Historically, the clinical case definition for cerebral malaria has lacked specificity. Further, treatments for cerebral malaria have been selected and administered on the basis of a very limited understanding of the mechanisms that are causing and/or contributing to brain injury in patients suffering from cerebral malaria. While several mechanisms have been proposed, due to resource limitations and lack of widespread diagnostic imaging, prevailing mechanisms have yet to be clearly identified. Understanding and diagnosing these mechanisms would allow doctors to tailor treatments to patients, by addressing and/or disrupting the specific mechanism that is the source of or will eventually cause brain injury.

The fundamental understanding of the pathogenesis of cerebral malaria is limited and there is no consensus about the pathogenesis. However, there are several postulated mechanisms for brain injury in cerebral malaria, including obstruction of cerebral microvascular flow, parasite-induced sequestration of infected and uninfected arythrocytes mediated through cytoadherence, rosette formation, autoagglutination and reduced red cell deformability, seizures, overt seizures, subtle and electrographic seizures, postictal state, impaired delivery of substrate, hypoglycaemia, anaemia, hypoxia, impaired perfusion, hypovolaemia, shock, acidosis, raised intracranial pressure and brain swelling, disruption of the blood-brain barrier, raised intracranial pressure, cerebral oedema, cytotoxic oedema, toxins, nitric oxide, reactive oxygen species, excitotoxins, malaria toxin and clotting intravascular coagulation as a minor mechanism.

Diagnosis of these mechanisms is difficult because imagining machines that are typically used to identify such mechanisms, such as magnetic resonance imaging (MRI) devices, are expensive, require large power inputs, and are typically non-portable.

SUMMARY

One example embodiment of the present disclosure includes a transcranial scanning system for identifying a neurologic-injury-mechanism, comprising a sensing wand comprising a transducer that produces and receives sound waves and a sound amplification component, the transducer generates a sound wave that is amplified by the sound amplification component to comprise an amplified sound wave when the sensing wand is passed over a head of a patent with cerebral malaria, the amplified sound wave reflects off of blood cells in blood vessels in the head of the patient and causes a change in pitch of the amplified sound wave creating an output sound wave responsive to a blood flow of the patient, the output sound wave is received by the transducer, a processor in communication with said sensing wand, and an output screen coupled to the sensing wand and the processor, the output screen displays in real time an output waveform corresponding to the output sound wave, wherein the processor identifies, based on characteristics of a repeating pattern displayed on the output waveform, a neurologic-injury-mechanism occurring within the patient.

Another example embodiment of the present disclosure includes a method of producing an image using a transcranial sensing device, the image for identifying a neurologic-injury-mechanism, the method comprising using a transcranial scanning device to scan a head portion of a patient diagnosed with cerebral malaria, wherein the transcranial scanning device includes a scanning component that measures sound waves that are reflected off of blood cells within a brain of the patient to indicate real-time conditions within the brain via an image of a waveform output, comparing the image of a waveform output of the patient to one or more images of injury mechanism waveforms that are each linked to a specific neurologic-injury-mechanism, wherein the one or more injury mechanism waveforms comprise variations relative to images of normal waveform outputs generated when scanning a healthy patient, matching the image of a waveform output to the image of a closest matching injury mechanism waveform of the one or more injury mechanism waveforms, and identifying the neurologic-injury-mechanism of the patient based upon the linked neurologic injury mechanism of the closest matching injury mechanism waveform.

Yet another example embodiment of the present disclosure includes a method of analyzing images using a transcranial sensing device to identify a neurologic-injury-mechanism, the method comprising identifying one or more images of injury mechanism waveforms that illustrate a repeating pattern of at least one of a peak systolic velocity value, an end-diastolic velocity value, and a diachrotic notch value associated with a specific injury mechanism, wherein the one or more images of injury mechanism waveforms correlate to an age and size of a patient, matching the one or more images of injury mechanism waveforms to at least one of a first injury mechanism comprising sequestration, a second injury mechanism comprising venous obstruction, a third injury mechanism comprising vasospasm, a fourth injury mechanism comprising hyperemia, and a fifth injury mechanism comprising low blood flow, generating a patient image comprising a repeating pattern of a cranial scan of the patient that is indicative of blood flow patterns including at least one of a peak systolic velocity value, an end-diastolic velocity value, and a diachrotic notch value to the one or more images of injury mechanism waveforms, comparing the patient image to the one or more images of injury mechanism waveforms, identifying the neurologic-injury-mechanism of the patient as one of the first, second, third, fourth and fifth injury mechanism based upon having a closest similarity to one or more images of injury mechanism waveforms based upon the matched neurologic injury mechanism.

BRIEF DESCRIPTION OF THE DRAWINGS

The foregoing and other features and advantages of the present disclosure will become apparent to one skilled in the art to which the present invention relates upon consideration of the following description of the invention with reference to the accompanying drawings, wherein like reference numerals refer to like parts unless described otherwise throughout the drawings and in which.

DETAILED DESCRIPTION

The present disclosure relates to method and apparatus for identifying a mechanism of neurologic injury in persons having cerebral malaria. More specifically, the present disclosure relates to identifying a mechanism of neurologic injury in persons having cerebral malaria using a transcranial sensing apparatus, such as a transcranial Doppler ultrasound, and identifying a treatment type based upon the mechanism that is identified.

Figure 1:
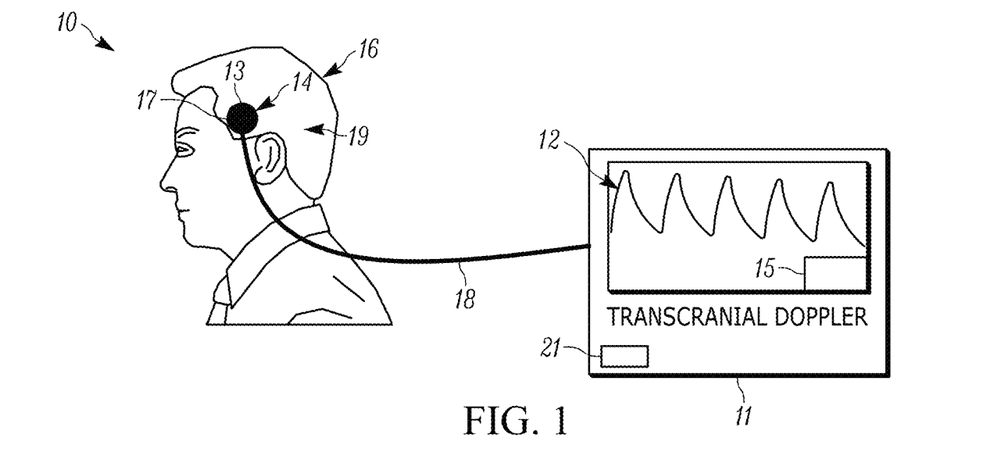
FIG. 1 is an example Transcranial Scanning Device (TSD) for use in identifying cerebral blood flow velocities in patients in accordance with one example embodiment of the present disclosure.

Illustrated in FIG. 1, is a first transcranial scanning device (TSD) 10. In one example embodiment, A first TSD 10 is a Transcranial Doppler Ultrasound device. An example of a suitable Transcranial Doppler Ultrasound device is—commercially available under part number Sonara Tek/NCM 117311, manufactured by Natus Neurology. The first TSD 10 comprises an imaging device 11 for displaying TSD spectra waveform 12 for use in real time. In one example embodiment, the TSD 10 comprises a handheld device 14 that is passed lightly over the skin in a scanning area 19 above a blood vessel (e.g., cerebral artery (MCA), basilar artery (BA), ipsilateral extracranial internal carotid artery, etc.) to assess the blood flow of a patient 16. In this illustrated example embodiment, the handheld scanning device 14 is in a wired communication 18 with the imaging device 11, which displays the TSD spectra waveform 12. In another example embodiment, the handheld device 14 is in wireless communication with the imaging device 11 via transceiver/receiver/transmitter 20, 22 as shown in FIG. 2 with regard to a second transcranial scanning device 10a.

Figure 2:
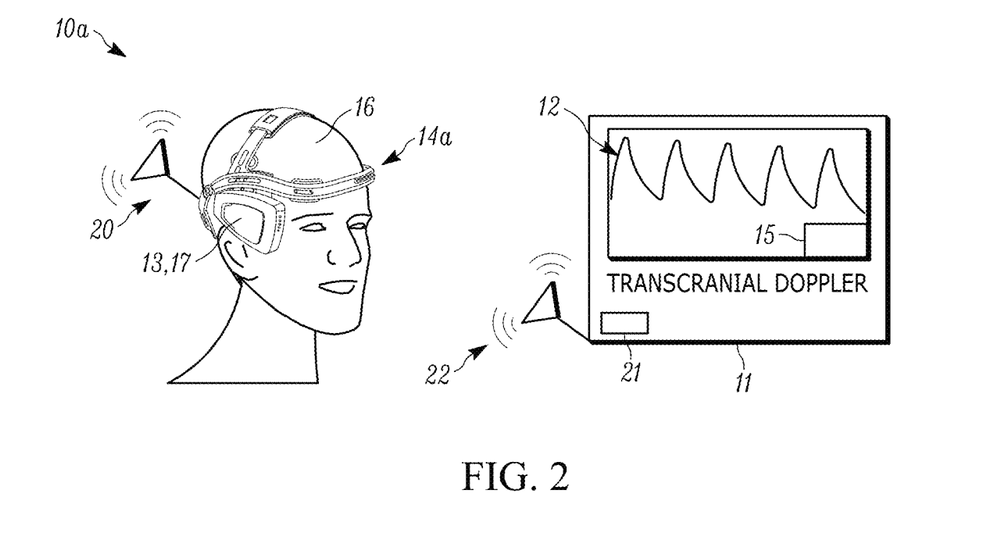
FIG. 2 is a second example Transcranial Scanning Device (TSD) for use in identifying cerebral blood flow velocities in patients in accordance with one example embodiment of the present disclosure.

In the illustrated example embodiment of FIG. 2, a second transcranial scanning device (TSD) 10a comprises a wearable device 14a that functions in a similar or same manner as the handheld device 14, except that the handheld device is replaced by automated readings of portable scanner 14a. The second and wearable TSD 10a is one of in wired communication 18 with the imaging device 11, or in wireless communication with the imaging device. In one example embodiment, the TSD 10, 10a comprises a transducer 13 and/or a sound amplification component. The TSD 10, 10a, through the transducer 13 or microphone, sends and receives sound waves that are amplified through circuit comprising the microphone. The sound waves from the scanner 14, 14a bounce off blood cells in the second scanner area 19 of the patient. The movement of blood cells (e.g., through the patient's veins and/or arteries) changes the pitch of the reflected sound waves produced by the scanner 14, 14a. For example, if there is no blood flow (e.g., the blood cells are not moving) the pitch transmitted back to the imaging device 11 does not change. The TSD 10, 10a are referred to interchangeably below as TSD 10.

In one example embodiment, the TSD 10 is a non-invasive ultrasound device used for real-time evaluation of the cerebral blood flow within the basal cerebral vessels, an example transcranial scanning device is the Transcranial Doppler (TCD) device. The TSD 10 is portable with examinations performed and interpreted at the patient's 16 bedside. The scanner 14, 14a takes a reading through transducer 13 or microphone 17 and generates a corresponding output signal, such as a sonogram and/or the TSD spectral waveform 12 that depicts low resistance waveforms with a sharp systolic upstroke 102a followed by a diachrotic notch 114 and stepwise deceleration 116 to end diastole 118 (see, for example, FIG. 3). Age and gender normal values for velocities measured by the TSD 10 in each cerebral vessel are known in the art. Furthermore, the TSD 10 is used to assess the physiological health of a particular vascular territory by measuring blood flow responses to changes in blood pressure.

The TSD 10 incorporates an algorithm 15 which is programmed to compare TSD spectra waveforms from a current patient to one or more TSD spectra waveforms corresponding to one or more injury mechanisms based on one or more inputs (e.g., the algorithm stores in a memory component of a controller 21 multiple TSD spectra waveforms), to provide for identification of injury mechanism of the patient. (See FIG. 1). In some example embodiments, the controller 21 comprises an electronic processor such as a microprocessor, central processing unit, including the memory component and/or the like.

Figure 3:
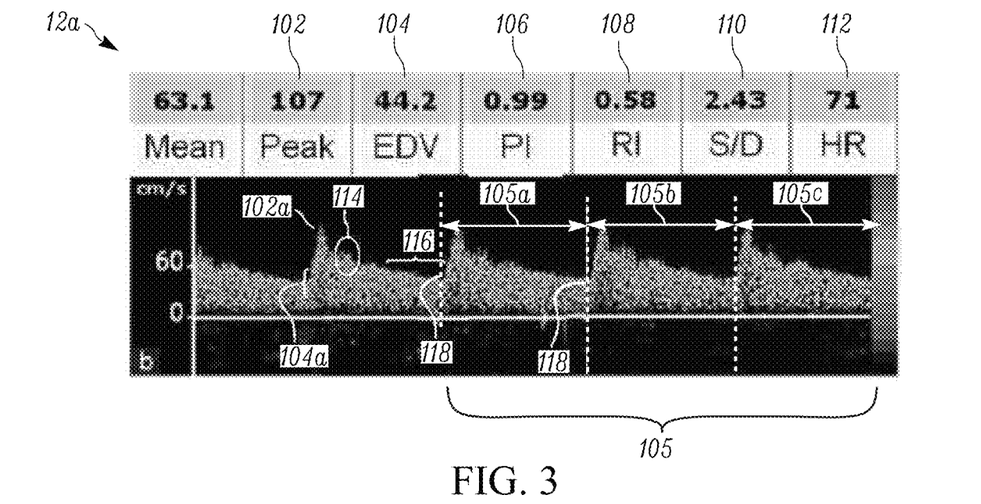
FIG. 3 is an example waveform generated by a Transcranial Scanning Device (TSD) in a normal or healthy patient in accordance with one example embodiment of the present disclosure.

In the illustrated example embodiment of FIG. 3, a normal spectral waveform/TSD spectra 100 shows the sharp systolic upstroke 102a and the stepwise deceleration 116 with positive end-diastolic flow. The variables noted on the example normal TSD spectra 100 are:

1) a peak systolic velocity 102 (PSV in cm/s), which is the first peak (systolic upstroke 102a) on the example normal TSD spectra waveform 12a from each cardiac cycle;
2) an end-diastolic velocity 104 (EDV in cm/s), which lies between 20% and 50% of the peak systolic velocity (PSV) 102a values;
3) a pulsatility index (PI) 106. A flow resistance is usually assessed by PI, to determine the flow resistance. PI is independent of the angle of insonation, has no unit, and a value more than 1.2 typically represents high resistance blood flow;
4) a resistance index (RI) 108 that is used to assess the flow resistance. It represents flow resistance distal to the site of insonation. Any value below 0.75 is typically normal;
5) a systolic diastolic ratio (S/D) 110, which represents the ratio between PSV and EDV; and
6) heart rate (HR) 112.

Additionally, the presence or absence of the dicrotic notch 114 is a variable that is considered in normal v. abnormal TCD spectra 12 readings.

In the illustrated example embodiment of FIG. 3, a repeating pattern comprising 105a, 105b, 105c is illustrated. The repeating pattern 105 begins and ends at the end diastolic velocity 118, although a locating or repetition in another embodiment, includes any fixed location (e.g., the peak systolic velocity 102a, the diachrotic notch 114a, etc.). The spectra waveform 12 comprises two or more units of the repeating pattern 105a-105c.

In some embodiments, the systolic and diastolic velocities (PSV and EDV) are measured at both the middle cerebral artery (MCA) and the basilar artery (BA), and a mean flow velocity (VM) at each is determined. Additionally, a Lindegaard Ratio which equals mean velocity in the MCA over a mean velocity in the ipsilateral extracranial internal carotid artery, is calculated for use in mechanism of injury identification.

Mechanism of neural injury associated with cerebral malaria and/or other viruses, or bacteria that cause mechanisms of injury that can be detected by changes to the TSD spectral waveform 12 output by the TSD 10 (e.g., that are indicative of changes to systolic blood pressure, diastolic blood pressure, an aortic valve closure time via the diachrotic notch 114). Additionally, the TSD spectral waveform 12 output by the TSD 10 will indicate if there are any abnormalities in the pulsatility of evaluated vessels, and indicate if there are alterations of measured blood flow velocities from expected values in both intra and extracranial vessels (e.g., via extracranial carotid flow, and the pulsatility index (PI) 106). In one or more example embodiments, though a single element measure (e.g., end diastolic velocity 118, the peak systolic velocity 102a, the diachrotic notch 114a, etc.) is identified as indicative of neurologic injury mechanism, it is the repeating pattern 105 illustrating the repetition of the element measure, rather than a single unit of the repeating pattern 105a, 105b, that is indicative of the neurologic injury mechanism.

The TSD 10 is used to identify mechanisms responsible for neurologic injury in children with cerebral malaria by identifying changes to expected (e.g., as seen in a normal healthy patient) TSD spectral waveforms 12.

Figure 4:
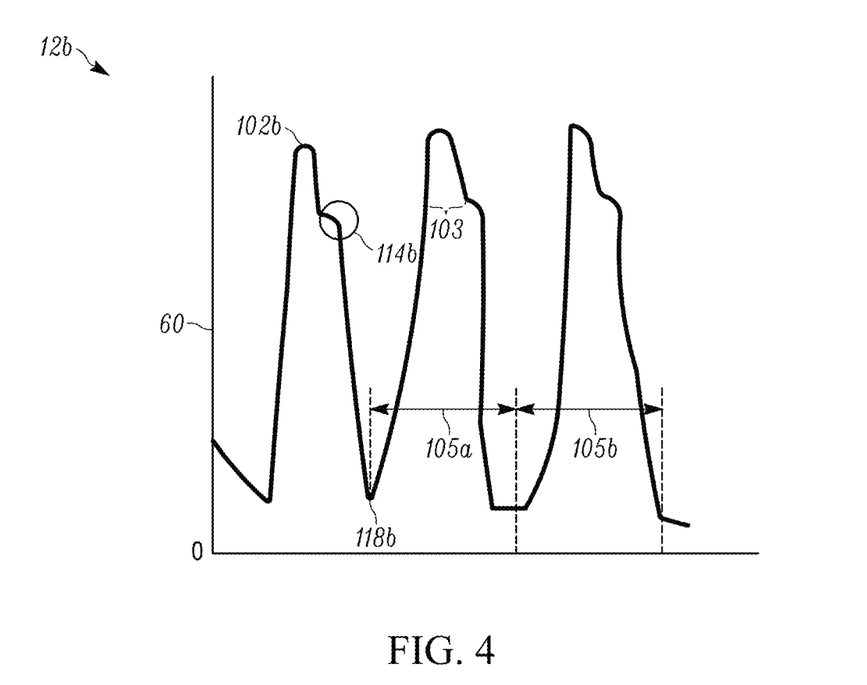
FIG. 4 illustrates an example waveform generated by a Transcranial Scanning Device (TSD) in a patient suffering a first injury mechanism in accordance with one example embodiment of the present disclosure.
Figure 5:
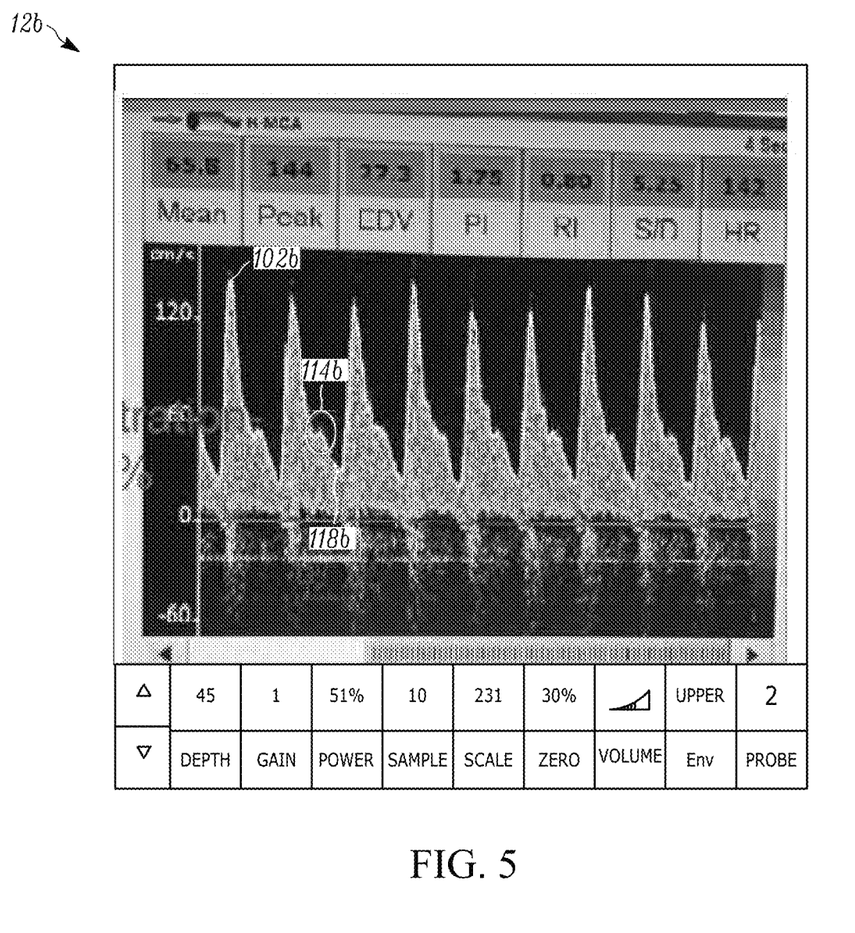
FIG. 5 is a second example waveform generated by a Transcranial Scanning Device (TSD) in a patient suffering a first injury mechanism in accordance with one example embodiment of the present disclosure.

There are several mechanisms for cerebral microcirculatory disturbances that have been identified. Example sequestration TSD spectral waveforms 12b of a first mechanism of neural injury comprising arterial sequestration are illustrated in FIGS. 4 and 5. Sequestration, both arterial and venous, occurs when infected parasitized red blood cells adhere to brain endothelium through binding receptors. The red blood cells remain in vascular space when sequestered, this leads to multiple local and downstream vascular effects. These vascular effects include vascular obstruction, which can cause reduced blood flow, hypo perfusion, hypo oxygenation, ischemia and acidosis. Sequestration can also cause capillary plugging, which is believed to be caused by a decreased deformability or increased stiffness of parasitized red blood cells and consequently plug capillaries with stiff red cells.

Capillary plugging is independent of endothelial cell adhesion molecules, the stiffness occurs because of insertion of parasite proteins into the red cell membrane and increased internal viscosity increased by rigid parasite. The first injury mechanism initially causes the TSD 10 to display the sequestration TSD waveform 12b because the patient 16 exhibits first early symptoms comprising normal systolic blood pressure 102b, low diastolic blood pressure 118b, a normal diachrotic notch 114b, normal extracranial carotid flow, and an elevated PI 106 (e.g., over 0.75). Herein, references to high, low, and normal are relative to an age determined normal systolic and diastolic blood pressures, dichotic notch, extracranial carotid flow, and/or PI.

The first injury mechanism then causes, once the first injury mechanism has advanced to first later symptoms, a second sequestration TSD waveform, which is similar to the sequestration TSD waveform 12b, except that the patient's 16 systolic blood pressure falling below normal 103 (illustrated in dashed lines), while the PI returns to the normal range (e.g., below 0.75). The TCD 10 generates the sequestration TSD waveform 12b as the first injury mechanism output that indicates, through indentifying the first symptoms, the first injury mechanism of neural injury is affecting the patient. A treatment that targets sequestration (e.g., targets the blockage caused by the sequestration in the patient's arteries) will be prescribed for the patient 16, as described in detail below. By eliminating and/or mitigating the injury causing mechanism the patient 16 will have better outcomes, and will suffer less brain injury.

Figure 6:
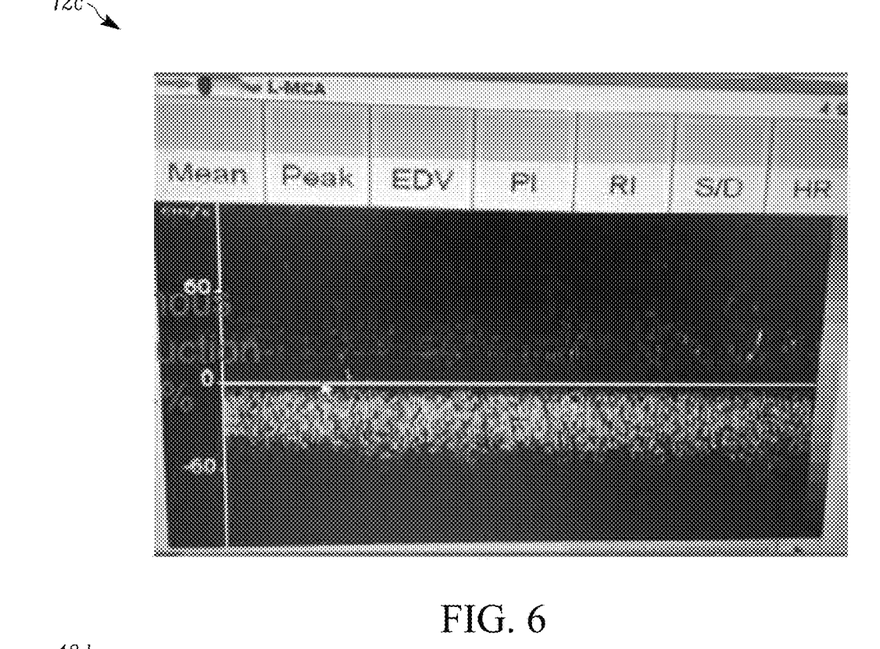
FIG. 6 is an example waveform generated by a Transcranial Scanning Device (TSD) in a patient suffering a second injury mechanism in accordance with one example embodiment of the present disclosure.

An example venous obstruction TSD waveform 12c of a second injury mechanism of neural injury is illustrated in FIG. 6. The second venous obstruction mechanism comprises venous obstruction. Venous obstruction occurs when the patients veins are obstructed in the same manner as described above with regard to arteries. For example, obstruction of postcapillary venules with sequestered red cells could lead to vascular congestion and increased brain volume. The second venous obstruction mechanism induces increased venous flow, which causes unclear readings below a threshold. For example, the systolic spike 102a, diastolic blood pressure 118, and the diachrotic notch 114, as shown in FIG. 3, are absent in the venous obstruction TSD waveform 12c.

The TSD 10 generates the venous obstruction TSD waveform 12c as the second injury mechanism output as shown in FIG. 6 that indicates, through indentifying the second symptoms, the second mechanism of neural injury is affecting the patient. In some example embodiments, the Lindegaard ratio is calculated, and considered, wherein the Lindegaard ratio is typically less than three (3) when the patient 16 is experiencing the second injury mechanism. A treatment that targets venous obstruction (e.g., targets the blockage in the patient's veins caused by the sequestration) will be prescribed for the patient 16, as described in detail below. By eliminating and/or mitigating the injury causing mechanism, the patient will have better outcomes, and will suffer less brain injury.

Figure 7:
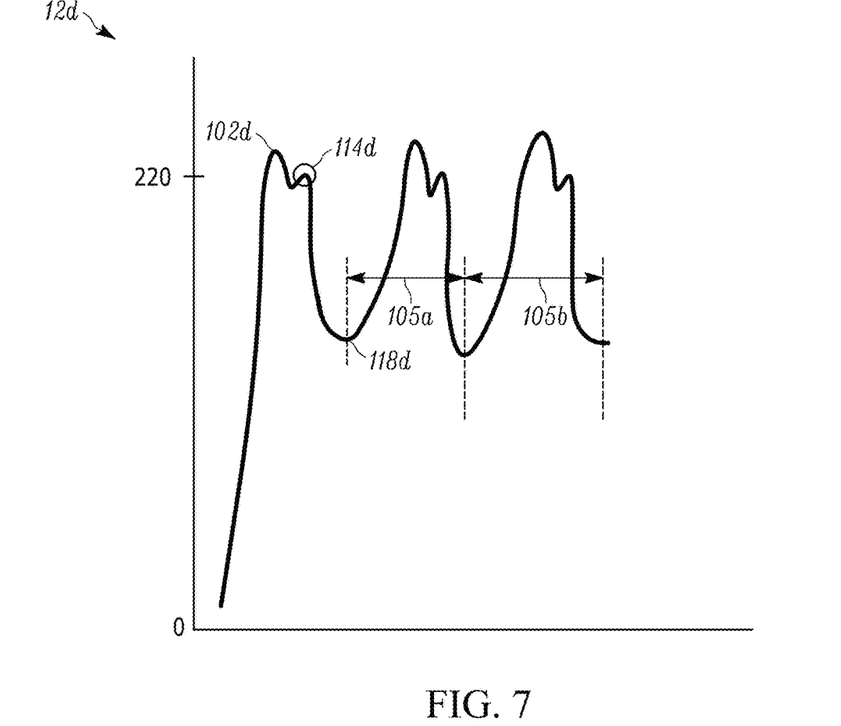
FIG. 7 illustrates an example waveform generated by a Transcranial Scanning Device (TSD) in a patient suffering a third injury mechanism in accordance with one example embodiment of the present disclosure.
Figure 8:
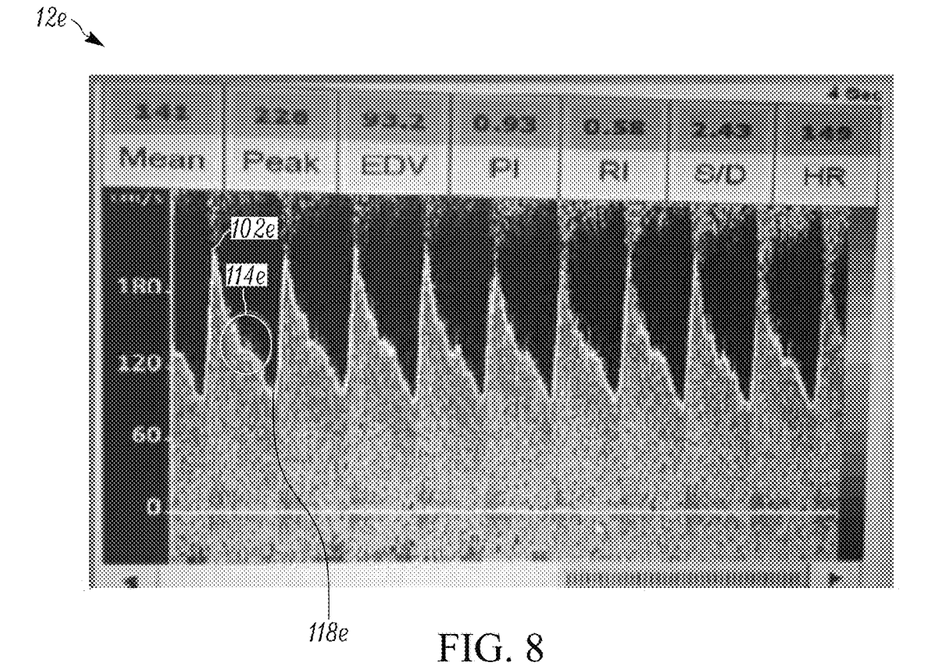
FIG. 8 is a second example waveform generated by a Transcranial Scanning Device (TSD) in a patient suffering a third injury mechanism in accordance with one example embodiment of the present disclosure.

An example cerebral vasoconstriction TSD waveform 12d and an example vasospasm TSD waveform 12e of a third injury mechanism of neural injury comprising cerebral vasoconstriction and/or vasospasms are illustrated in FIGS. 7 and 8, respectively. The third injury mechanism comprises cerebral vasoconstriction and/or vasospasms. In one example embodiment, vasoconstriction occurs when there is impaired nitric oxide (NO) bioavailability and L-arginine reversible endothelial dysfunction contribute to signaling that veins should constrict. The third injury mechanism causes a patient to exhibit third symptoms that present on the cerebral vasoconstriction TSD waveform 12d and/or the vasospasm TSD waveform 12e as comprising elevated systolic blood pressure 102d, 102e, elevated diastolic blood pressure 118d, 118e, a normal diachrotic notch 114d, 114e, normal extracranial carotid flow, and a low PI, as illustrated in FIGS. 7 and 8. The TSD 10 generates the cerebral vasoconstriction TSD waveform 12d and the vasospasm TSD waveform 12e as a third injury mechanism output that indicates, through indentifying the third symptoms, the third injury mechanism of neural injury is affecting the patient. In some example embodiments, the Lindegaard ratio is calculated, and considered, wherein the Lindegaard ratio is typically greater than or equal to three (3) when the patient 16 is experiencing the third mechanism of injury. A treatment that targets vasoconstriction and/or vasospasms (e.g., proscribing a vasodilator, or the like to reverse the vasoconstriction, and/or a smooth muscle relaxer that prevents or reduces vasospasms) will be prescribed for the patient 16, as described in detail below. By eliminating and/or mitigating the injury causing mechanism based upon identification of the mechanism, the patient will have better outcomes, and will suffer less brain injury.

Figure 9:
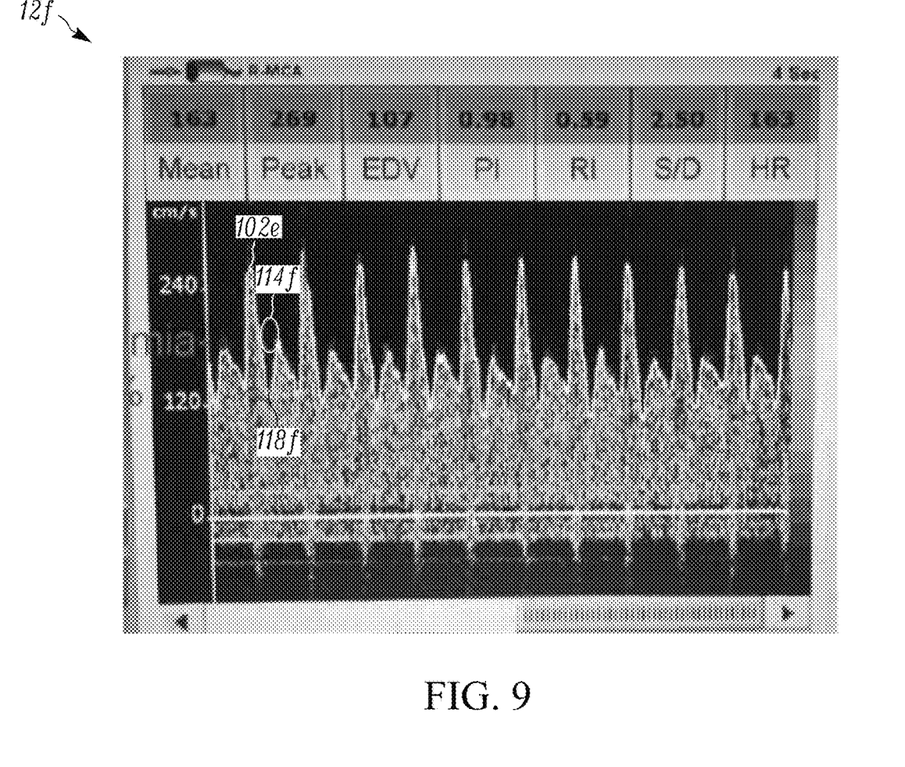
FIG. 9 is an example waveform generated by a Transcranial Scanning Device (TSD) in a patient suffering a fourth injury mechanism in accordance with one example embodiment of the present disclosure.
Figure 10:
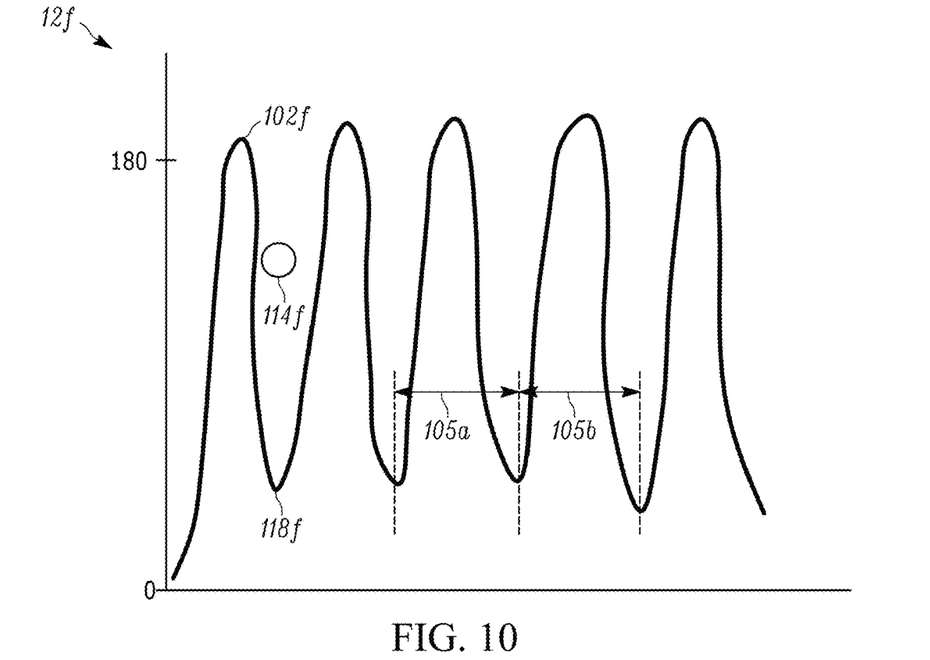
FIG. 10 illustrates a second example waveform generated by a Transcranial Scanning Device (TSD) in a patient suffering a fourth injury mechanism in accordance with one example embodiment of the present disclosure.

Example hyperemia TSD waveforms 12f of a fourth injury mechanism of neural injury comprising hyperemia are illustrated in FIGS. 9-10. The fourth injury mechanism comprises hyperemia. In one example embodiment, anemia, seizures, and fever that are common in children with cerebral malaria lead to increased cerebral blood flow (hyperemia) that contributes to increased cerebral volume in children with cerebral malaria (e.g., through vasogenic edema). The fourth injury mechanism causes the hyperemia TSD waveform 12f to indicate the patient 16 is exhibiting fourth symptoms comprising elevated systolic blood pressure 102f, normal diastolic blood pressure 118f, a loss of the diachrotic notch 114f (the circle 114f indicates where the notch should be), increased extracranial carotid flow, and an increased PI. Additionally, the fourth injury mechanism will cause the patient to exhibit a greater than 10% differential in bilateral flow velocities. In some example embodiments, the Lindegaard ratio is calculated, and considered, wherein the Lindegaard ratio is typically less than three (3) when the patient 16 is experiencing the fourth mechanism of injury. The TSD 10 generates the hyperemia TSD waveform 12f as the fourth injury mechanism that indicates the fourth mechanism of neural injury is affecting the patient. A treatment that targets hyperemia (e.g., prescribing an anti-inflammatory or the like to prevent the vasogenic edema) will be prescribed for the patient 16, as described in detail below. By eliminating and/or mitigating the injury causing mechanism based upon identification of the mechanism the patient will have better outcomes, and will suffer less brain injury.

Figure 11:
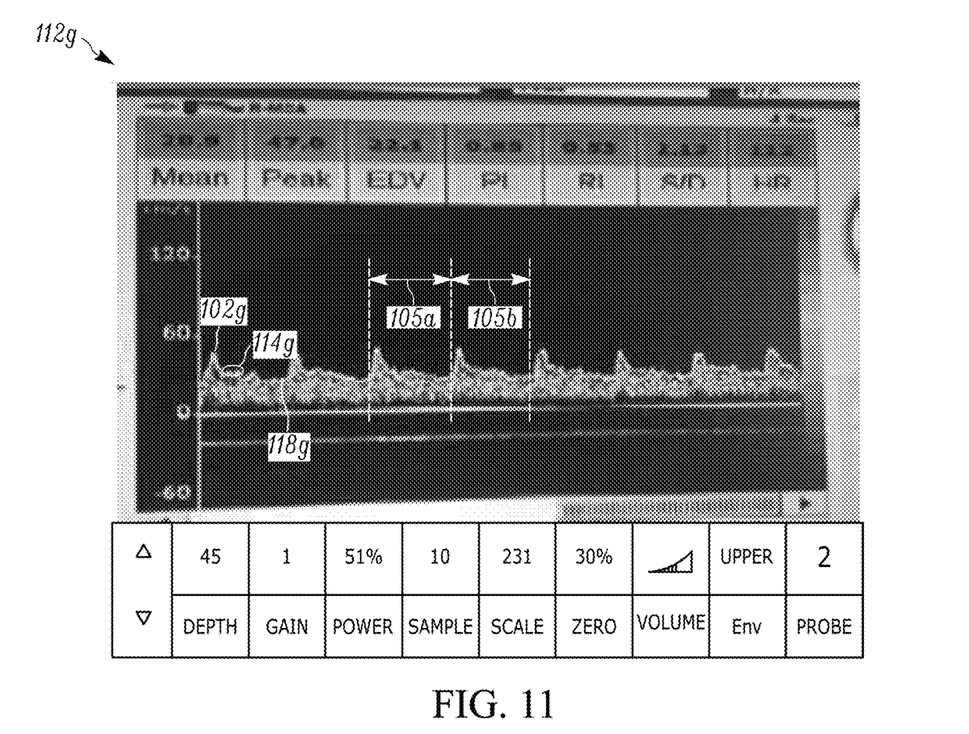
FIG. 11 is an example waveform generated by a Transcranial Scanning Device (TSD) in a patient suffering a fifth injury mechanism in accordance with one example embodiment of the present disclosure.

An example low cerebral blood flow TSD waveform 12g of a fifth injury mechanism of neural injury comprising low cerebral blood flow is illustrated in FIG. 11. The fifth mechanism comprises low cerebral blood flow. The fifth mechanism can cause brain cell death and cytotoxic shock. The fifth mechanism causes a patient to exhibit fifth symptoms that present on the low cerebral blood flow TSD waveform 12g as comprising lowered systolic blood pressure 102g, lowered diastolic blood pressure 118g, a normal diachrotic notch 114g, and a normal PI. The TSD 10 generates the fifth mechanism output as the low cerebral blood flow TSD waveform 12g, which indicates the fifth injury mechanism of neural injury is affecting the patient. In some example embodiments, the Lindegaard ratio is calculated, and considered, wherein the Lindegaard ratio is typically less than three (3) when the patient 16 is experiencing the fifth mechanism of injury. A treatment that targets low cerebral blood flow will be prescribed for the patient 16, as described in detail below. By eliminating and/or mitigating the injury causing mechanism based upon identification of said mechanism, the patient will have better outcomes, and will suffer less brain injury.

A chart is provided below to summarize the various aspects of each mechanism of injury, wherein "N" indicates normal, and an arrow pointing upward or downward indicates the aspect in the corresponding vertical column is high, or low, respectively:

| TSD waveform output | PSV at MCA | EDV at MCA | VM at MCA | Pulsatility index (PI) | Lindegaard ratio | Dichrotic notch |
|---|---|---|---|---|---|---|
| Second Mechanism of Injury: Venous obstruction | N | ↓ | ↓ | ↑ | <3 | Present |

-continued

| TSD waveform output | PSV at MCA | EDV at MCA | VM at MCA | Pulsatility index (PI) | Lindegaard ratio | Dichrotic notch |
|---|---|---|---|---|---|---|
| Third Mechanism of Injury: Vasospasm | ↑ | ↑ | ↑ | ↓ | ≥3 | Present |
| Fourth Mechanism of Injury: Hyperemia | ↑ | ↑ | ↑ | N | <3 | Absent |
| Fifth Mechanism of Injury: Low flow | ↓ | ↓ | ↓ | N | <3 | Present |

MCA: middle cerebral artery; BA: basilar artery; PSV: systolic flow velocity; EDV: diastolic flow velocity; VM: mean flow velocity.

Figure 12:
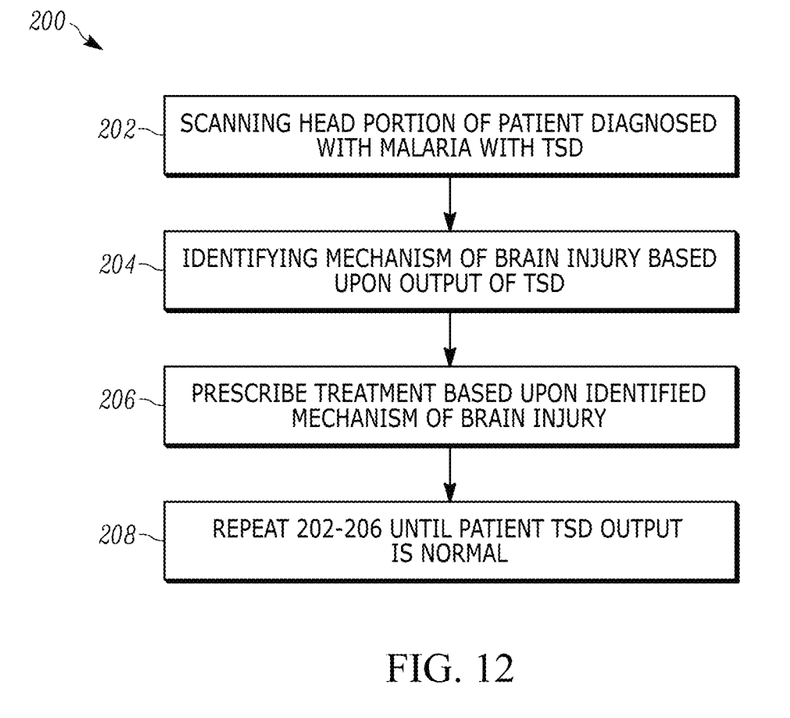
FIG. 12 is a flow diagram of a method of using a Transcranial Scanning Device (TSD) to identify and treat malarial cerebral injury in accordance with one example embodiment of the present disclosure.

In FIG. 12, an example method 200 of using the TSD 10 to detect and identify mechanism of brain injury in malarial patients is illustrated. At 202, a head portion of a patient diagnosed with cerebral malaria is scanned with the TSD 10. At 204, a mechanism of brain injury is identified based upon symptoms indicated by the TSD spectra waveform 12b-12g output of the TSD 10. At 206, a treatment is prescribed to address the mechanism identified by the TSD output. At 208, steps 202-206 are repeated until the TSD spectra waveform 12 output is the normal TSD spectra waveform 12a.

Figure 13:
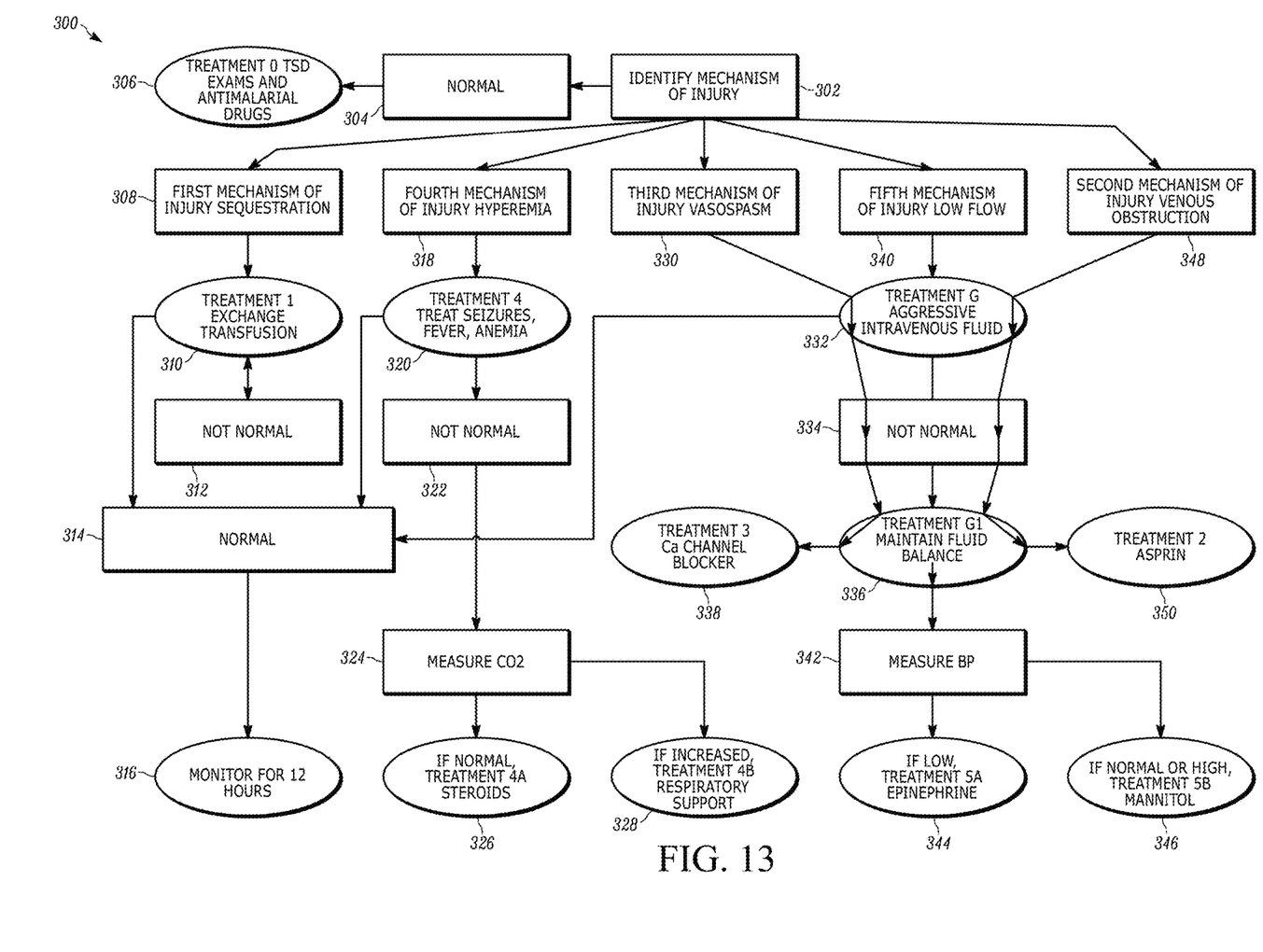
FIG. 13 is a second flow diagram of a method of using a Transcranial Scanning Device (TSD) to identify and treat malarial cerebral injury in accordance with one example embodiment of the present disclosure.

In FIG. 13, an example method 300 of using the TSD 10 to identify mechanisms of brain injury in malarial patients and identify one or more treatments based upon the identified brain injury is illustrated. At 302, using the TSD 10 a mechanism of injury is identified. At 304, the malarial patent 16 is identified as having the normal TSD waveform 12a. At 306, the malarial patient having the normal TSD waveform 12a is assigned treatment 0, which include hourly, daily, or weekly TSD 10 exams and antimalarial drugs. At 308, the malarial patient 16 is identified as a sequestration patient by exhibiting the sequestration TSD waveform 12a, and thus the first injury mechanism. At 310, the sequestration patient 16 is assigned treatment 1, which comprises an exchange transfusion. At 312, the exchange transfusion continues while the sequestration patient remains not normal (e.g., having the TSD waveform 12b). At 314, once the sequestration patient 16 has the normal TSD waveform 12a the exchange transfusion is stopped. At 316, the sequestration patient having the normal TSD waveform 12a is monitored for 12 hours, and if said sequestration patient remains normal, the sequestration patient is assigned Treatment 0.

At 318, the malarial patient 16 is identified as a hyperemia patient by exhibiting the hyperemia TSD waveform 12f, and thus the fourth mechanism of injury. At 320, the hyperemia patient 16 is assigned treatment 4, which comprises treating fevers, seizures, and anemia. At 322, treatment 4 is finished and the hyperemia patient remains not normal (e.g., having the TSD waveform 12f). At 324, the not normal hyperemia patient's 16 $CO_2$ levels are measured. At 326, the not normal hyperemia patient's 16 $CO_2$ levels are normal, and the hyperemia patient is administered treatment 4a, which, for example, comprises steroids. At 328, the not normal hyperemia patient's 16 $CO_2$ levels are increased, and the not normal hyperemia patient is administered treatment 4b, which, for example, comprises respiratory support. At 314, treatment 4 is finished and the hyperemia patient 16 exhibiting the normal TSD waveform 12a is assigned Treatment 0.

At 330, 340, and 348 the malarial patient 16 is identified as one of a vasoconstricted, low flow, or venous obstructed patient because they exhibit the vasospasm or vasoconstriction TSD waveform 12d-12e, and thus the third mechanism of injury, the low flow TSD waveform 12g and thus the fifth mechanism of injury, or the venous obstruction TSD waveform 12c and thus the second mechanism of injury, respectively. At 332, the vasoconstricted, low flow, or venous obstructed patient 16 is assigned treatment G, which comprises, for example, administering aggressive intravenous fluids (e.g., administering fluids at 40-100 milliters per kilogram of patient body weight). At 314, once the vasoconstricted, low flow, or venous obstructed patient 16 has the normal TSD waveform 12 treatment G is stopped. The vasoconstricted, low flow, or venous obstructed patient having the normal TSD waveform 12a is assigned Treatment 0.

At 322, treatment G is finished and the patient 16 remains not normal (e.g., having a TSD waveform 12c-12e, 12g). At 336, the vasoconstricted, low flow, or venous obstructed patient is assigned treatment G1, which, for example, comprises maintaining a fluid balance.

At 338, wherein the vasoconstricted patient 16 was assigned the third mechanism of injury, the vasoconstricted patient, in addition to treatment G1 is administered treatment 3, which comprises, for example, a calcium channel blocker. At 342, wherein the low flow patient 16 was assigned the fifth mechanism of injury, the low flow patient, in addition to treatment G1 has their blood pressure measured. At 344, the low flow patient's blood pressure is low, the low flow patient is given treatment 5a, which comprises, for example, a epinephrine. At 346, the low flow patient's blood pressure is normal or high, the low flow patient is given treatment 5b, which comprises, for example, mannitol. At 350, wherein the venous obstruction patient 16 was assigned the second mechanism of injury, the venous obstruction patient, in addition to treatment G1 is administered treatment 2, which comprises, for example, aspirin.

Multiple mechanisms of injury contribute to neurologic injury, but a single predominant mechanism of injury can be identified for most children. Treatment of the predominant mechanism of injury will limit bad outcomes in children with cerebral malaria, by mitigating the actual injury mechanism rather than generally treating the symptoms that could and are caused by differing mechanisms of injury.

In the foregoing specification, specific embodiments have been described. However, one of ordinary skill in the art appreciates that various modifications and changes can be made without departing from the scope of the disclosure as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The disclosure is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having,"

"includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected or in contact, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

I claim:

1. A method of analyzing images using a transcranial sensing device to identify a neurologic-injury-mechanism, the method comprising:
   identifying five images of injury mechanism waveforms generated by the transcranial sensing device that illustrate a repeating pattern of at least one of a peak systolic velocity value, an end-diastolic velocity value, and a diachrotic notch value associated with a specific injury mechanism, wherein the one or more images of injury mechanism waveforms correlate to an age of a patient, the transcranial sensing device in communication with a processor;
   matching each of the five images of injury mechanism waveforms, utilizing the processor, to a first injury mechanism comprising sequestration, a second injury mechanism comprising venous obstruction, a third injury mechanism comprising vasospasm, a fourth injury mechanism comprising hyperemia, and a fifth injury mechanism comprising low blood flow, respectively;
   generating a patient image comprising a repeating pattern of a cranial scan of the patient generated by the transcranial sensing device that is indicative of blood flow patterns including at least one of a peak systolic velocity value, an end-diastolic velocity value, and a diachrotic notch value to the five images of injury mechanism waveforms;
   comparing the patient image to the five images of injury mechanism waveforms stored on a controller of the transcranial sensing device; and
   identifying the neurologic-injury-mechanism of the patient as one of the first, second, third, fourth and fifth injury mechanism based upon having a closest similarity to five images of injury mechanism waveforms based upon the matched neurologic injury mechanism.

2. The method of claim 1, the matching the one or more images of injury mechanism waveforms comprising at least one of:
   matching a first image that indicates that the patient has normal systolic blood pressure, low diastolic blood pressure, a normal diachrotic notch, normal extracranial carotid flow, and an elevated pulsatility index to sequestration; and
   matching a second image that indicates that the patient has increased venous flow and lacks systolic blood pressure, diastolic blood pressure, and a diachrotic notch to venous obstruction.

3. The method of claim 1, the matching the one or more images of injury mechanism waveforms comprising at least one of:
   matching a third image that indicates that the patient has elevated systolic blood pressure, elevated diastolic blood pressure, a normal diachrotic notch, normal extracranial carotid flow, and a low pulsatility index to vasoconstriction; and
   matching a fourth image that indicates that the patient has elevated systolic blood pressure, normal diastolic blood pressure, a loss of the diachrotic notch, increased extracranial carotid flow, and an increased pulsatility index to hyperemia.

4. The method of claim 1, the matching the one or more images of injury mechanism waveforms comprising matching a fifth image that indicates that the patient has lowered systolic blood pressure, lowered diastolic blood pressure, a normal diachrotic notch, and a normal pulsatility index to low cerebral blood flow.

5. The method of claim 1 comprising identifying a type of treatment based upon identifying the neurologic-injury-mechanism of the patient as one of the first, second, third, fourth and fifth injury mechanism neurologic-injury-mechanism of the patient.

6. The method of claim 5 comprising utilizing the processor of the transcranial sensing device to identify the type of treatment.

7. The method of claim 5 comprising presenting the identified type of treatment on an output screen of the transcranial sensing device.

8. The method of claim 1 wherein the transcranial sensing device comprises a Transcranial Doppler Ultrasound Device.

9. The method of claim 1, the matching the one or more images of injury mechanism waveforms comprising utilizing a processor of the transcranial sensing device to pattern match the cranial scan to the one or more images of injury mechanism waveforms.

10. The method of claim 1, receiving the cranial scan of the patient from a sensing wand of transcranial sensing device, the sensing wand comprising a transducer that produces and receives sound waves and a sound amplification component that amplifies received sound waves.

11. A method of analyzing images using a transcranial sensing device to identify a neurologic-injury-mechanism, the method comprising:
- identifying five images of injury mechanism waveforms that illustrate a repeating pattern of at least one of a peak systolic velocity value, an end-diastolic velocity value, and a diachrotic notch value associated with a specific injury mechanism, wherein the one or more images of injury mechanism waveforms correlate to an age and size of a patient;
- matching each of the five images of injury mechanism waveforms, utilizing the processor, to a first injury mechanism comprising sequestration, a second injury mechanism comprising venous obstruction, a third injury mechanism comprising vasospasm, a fourth injury mechanism comprising hyperemia, and a fifth injury mechanism comprising low blood flow, respectively;
- generating a patient image comprising a repeating pattern of a cranial scan of the patient that is indicative of blood flow patterns including at least one of a peak systolic velocity value, an end-diastolic velocity value, and a diachrotic notch value to the five images of injury mechanism waveforms;
- comparing the patient image to the five images of injury mechanism waveforms; and
- utilizing the processor of the transcranial sensing device to identify the neurologic-injury-mechanism of the patient as one of the injury mechanism based upon pattern matching having a closest similarity to one of the five images of injury mechanism waveforms based upon the matched neurologic injury mechanism.

12. The method of claim 11, the matching comprising assigning the first injury mechanism to the image of the injury mechanism waveform indicating sequestration, the second injury mechanism to the image of the injury mechanism waveform indicating venous obstruction, the third injury mechanism to the image of the injury mechanism waveform indicating vasospasm, the fourth injury mechanism to the image of the injury mechanism waveform indicating hyperemia, and the fifth injury mechanism to the image of the injury mechanism waveform indicating low blood flow.

13. The method of claim 11 comprising identifying a type of treatment based upon identifying the neurologic-injury-mechanism of the patient as one of the first, second, third, fourth and fifth injury mechanism neurologic-injury-mechanism of the patient.

14. The method of claim 11 comprising utilizing a processor of the transcranial sensing device to identify a type of treatment based upon identifying the neurologic-injury-mechanism of the patient as one of the first, second, third, fourth and fifth injury mechanism neurologic-injury-mechanism of the patient.

15. The method of claim 11 comprising presenting the type of treatment on an output screen of the transcranial sensing device.

16. The method of claim 11, the matching the five images of injury mechanism waveforms comprising utilizing a processor of the transcranial sensing device, the processor for:
- identifying a first image that indicates that the patient has normal systolic blood pressure, low diastolic blood pressure, a normal diachrotic notch, normal extracranial carotid flow, and an elevated pulsatility index, and matching the first image to the first injury mechanism;
- identifying a second image that indicates that the patient has increased venous flow and lacks systolic blood pressure, diastolic blood pressure, and a diachrotic notch, and matching the second image to the second injury mechanism;
- identifying a third image that indicates that the patient has elevated systolic blood pressure, elevated diastolic blood pressure, a normal diachrotic notch, normal extracranial carotid flow, and a low pulsatility index, and matching the third image to the third injury mechanism; and
- identifying a fourth image that indicates that the patient has elevated systolic blood pressure, normal diastolic blood pressure, a loss of the diachrotic notch, increased extracranial carotid flow, and an increased pulsatility index and matching the fourth image to the fourth injury mechanism.

17. The method of claim 11, the matching the one or more images of injury mechanism waveforms comprising utilizing a processor of the transcranial sensing device, the processor for:
- identifying a fifth image that indicates that the patient has lowered systolic blood pressure, lowered diastolic blood pressure, a normal diachrotic notch, and a normal pulsatility index, and matching the fifth image to low cerebral blood flow.

18. The method of claim 11, further comprising receiving the cranial scan of the patient from a sensing wand of transcranial sensing device, the sensing wand comprising a transducer that produces and receives sound waves and a sound amplification component.

19. The method of claim 11, the identifying the five images of injury mechanism waveforms comprising accessing the five images of injury mechanism waveforms stored in a controller of the transcranial sensing device.

20. A method of analyzing images using a transcranial sensing device to identify a neurologic-injury-mechanism, the method comprising:
- identifying five images of injury mechanism waveforms stored on a controller of the transcranial sensing device, the five images of injury mechanism waveforms illustrate a repeating pattern of at least one of a peak systolic velocity value, an end-diastolic velocity value, and a diachrotic notch value associated with a specific injury mechanism, wherein the one or more images of injury mechanism waveforms correlate to an age and size of a patient;
- matching each of the five images of injury mechanism waveforms, utilizing the processor, to a first injury mechanism comprising sequestration, a second injury mechanism comprising venous obstruction, a third injury mechanism comprising vasospasm, a fourth injury mechanism comprising hyperemia, and a fifth injury mechanism comprising low blood flow, respectively;
- generating a patient image comprising a repeating pattern of a cranial scan of the patient obtained from a sensing wand of the transcranial sensing device, the cranial scan is indicative of blood flow patterns including at least one of a peak systolic velocity value, an end-diastolic velocity value, and a diachrotic notch value to the one or more images of injury mechanism waveforms;
- comparing the patient image to the five images of injury mechanism waveforms;
- identifying the neurologic-injury-mechanism of the patient as one of the first, second, third, fourth and fifth injury mechanism based upon having a closest similarity to the five images of injury mechanism waveforms based upon the matched neurologic injury mechanism;

utilizing a processor of the transcranial sensing device to identify a type of treatment based upon the identified neurologic-injury-mechanism of the patient as one of the first, second, third, fourth and fifth injury mechanism; and presenting the type of treatment on an output screen of the transcranial sensing device.

* * * * *